(12) United States Patent
Otiaba et al.

(10) Patent No.: US 11,793,955 B2
(45) Date of Patent: Oct. 24, 2023

(54) AEROSOLIZABLE SUBSTRATE MATERIAL DETECTION SYSTEM AND METHOD FOR A VAPOR PROVISION SYSTEM

(71) Applicant: NICOVENTURES TRADING LIMITED, London (GB)

(72) Inventors: Kenny Otiaba, London (GB); David Leadley, London (GB)

(73) Assignee: Nicoventures Trading Limited, London (GB)

( * ) Notice: Subject to any disclaimer, the term of this patent is extended or adjusted under 35 U.S.C. 154(b) by 453 days.

(21) Appl. No.: 15/733,224

(22) PCT Filed: Nov. 20, 2018

(86) PCT No.: PCT/GB2018/053358
§ 371 (c)(1),
(2) Date: Jun. 11, 2020

(87) PCT Pub. No.: WO2019/115996
PCT Pub. Date: Jun. 20, 2019

(65) Prior Publication Data
US 2020/0352245 A1    Nov. 12, 2020

(30) Foreign Application Priority Data

Dec. 13, 2017  (GB) ..................... 1720787

(51) Int. Cl.
*A24F 47/00*    (2020.01)
*A61M 15/06*    (2006.01)
(Continued)

(52) U.S. Cl.
CPC ............. *A61M 15/06* (2013.01); *A24F 40/42* (2020.01); *A24F 40/51* (2020.01); *A24F 40/53* (2020.01);
(Continued)

(58) Field of Classification Search
CPC .......... A24F 40/50; A24F 40/51; A24F 40/53; A61M 2205/3306
See application file for complete search history.

(56) References Cited

U.S. PATENT DOCUMENTS 6,247,775 B1    6/2001 Walker
2005/0151764 A1    7/2005 Grady et al.
(Continued)

FOREIGN PATENT DOCUMENTS

CA    3039850 A1    4/2018
CN    201731916 U    2/2011
(Continued)

OTHER PUBLICATIONS

International Preliminary Reporton Patentability for Application No. PCT/GB2018/053358, dated Feb. 21, 2020, 10 pages.
(Continued)

*Primary Examiner* — Eric Yaary
(74) *Attorney, Agent, or Firm* — Patterson Thuente P.A.

(57) ABSTRACT

A vapor provision system includes a reservoir defining a storage volume to hold aerosolizable substrate material; and an aerosolizable substrate material detection system including an optical source located externally of the reservoir and operable to emit light into the storage volume; an optical detector located externally of the reservoir and operable to detect light emitted by the optical source that has traversed an optical path through the storage volume; and a controller configured to determine a characteristic of light detected by the optical detector and deduce information regarding a depth of aerosolizable substrate material in the storage volume from the determined characteristic of the light.

13 Claims, 6 Drawing Sheets

(51) Int. Cl.
  *A24F 40/53* (2020.01)
  *A24F 40/42* (2020.01)
  *A24F 40/51* (2020.01)
  *G01V 8/12* (2006.01)
  *A24F 40/10* (2020.01)
  *A24F 40/20* (2020.01)

(52) U.S. Cl.
  CPC ............... *G01V 8/12* (2013.01); *A24F 40/10* (2020.01); *A24F 40/20* (2020.01)

(56) References Cited

U.S. PATENT DOCUMENTS

| | | | |
|---|---|---|---|
| 2011/0102796 A1 | 5/2011 | Shang et al. | |
| 2014/0060554 A1* | 3/2014 | Collett | A24F 40/51 |
| | | | 392/386 |
| 2016/0302488 A1* | 10/2016 | Fernando | A24F 40/51 |
| 2016/0345628 A1 | 12/2016 | Sabet | |
| 2017/0086498 A1* | 3/2017 | Daryani | A24F 40/40 |
| 2017/0304545 A1* | 10/2017 | Biei | G06V 10/143 |
| 2017/0340010 A1 | 11/2017 | Bilat et al. | |
| 2017/0347710 A1* | 12/2017 | Hon | A61M 11/042 |
| 2018/0098574 A1* | 4/2018 | Sur | A24F 40/53 |
| 2018/0332895 A1* | 11/2018 | Li | A61M 11/042 |

FOREIGN PATENT DOCUMENTS

| | | |
|---|---|---|
| CN | 205865990 U | 1/2017 |
| CN | 107183784 A | 9/2017 |
| DE | 29705889 U1 | 8/1997 |
| EP | 3357360 A2 | 8/2018 |
| GB | 2533652 A | 6/2016 |
| JP | H0814989 A | 1/1996 |
| JP | 2014029278 A | 2/2014 |
| WO | WO-2014066730 A1 | 5/2014 |
| WO | WO-2016101202 A1 | 6/2016 |
| WO | WO-2016101203 A1 | 6/2016 |
| WO | WO-2016112542 A1 | 7/2016 |

OTHER PUBLICATIONS

International Search Report and Written Opinion for Application No. PCT/GB2018/053358, dated Feb. 4, 2019, 15 pages.
Office Action For Canadian Application No. 3,085,764, dated Aug. 27, 2021, 9 pages.

* cited by examiner

AEROSOLIZABLE SUBSTRATE MATERIAL DETECTION SYSTEM AND METHOD FOR A VAPOR PROVISION SYSTEM

PRIORITY CLAIM

The present application is a National Phase entry of PCT Application No. PCT/GB2018/053358, filed Nov. 20, 2018, which claims priority from GB Patent Application No. 1720787.9, filed Dec. 13, 2017, which is hereby fully incorporated herein by reference.

TECHNICAL FIELD

The present disclosure relates to a system and a method for detecting aerosolizable substrate material in a reservoir of an electronic vapor provision system such as a device using heating to release compounds for substrate materials, or an e-cigarette.

BACKGROUND

Vapor provision systems such as electronic cigarettes may operate by generating vapor for user inhalation from a supply of source liquid. Techniques for vapor generation include heating the liquid with a resistive or inductive heating element or feeding liquid to a vibrating perforated membrane. The source liquid is typically held in a reservoir as free liquid or within an absorbent matrix such as cotton wadding. When the liquid has been consumed, a new supply is required to continue vapor production. Some systems are wholly disposable so that the user simply replaces the complete system when the liquid is exhausted. Other systems allow the user to refill the reservoir, or to replace a component of the system that includes the reservoir with a new component containing a fresh supply of liquid. In some systems the reservoir is an internal component so that its contents cannot readily be observed during use of the system.

Accordingly, arrangements for detecting, measuring or monitoring the contents of a liquid reservoir in a vapor provision system are of interest.

SUMMARY

According to a first aspect of some embodiments described herein, there is provided a vapor provision system comprising: a reservoir defining a storage volume to hold aerosolizable substrate material; and an aerosolizable substrate material detection system comprising: an optical source located externally of the reservoir and operable to emit light into the storage volume; an optical detector located externally of the reservoir and operable to detect light emitted by the optical source that has traversed an optical path through the storage volume; and a controller configured to determine a characteristic of light detected by the optical detector and deduce information regarding a depth of aerosolizable substrate material in the storage volume from the determined characteristic of the light.

According to a second aspect of some embodiments described herein, there is provided an aerosolizable substrate material detection system for a vapor provision system, comprising: an optical source operable to emit light into a storage volume of a reservoir from a location external to the reservoir, the storage volume for holding aerosolizable substrate material; an optical detector operable to detect, at a location external to the reservoir, light emitted by the optical source that has traversed an optical path through the storage volume; and a controller configured to determine a characteristic of light detected by the optical detector and deduce information regarding a depth of aerosolizable substrate material in the storage volume from the determined characteristic of the light.

According to a third aspect of some embodiments described herein, there is provided a control unit for a vapor provision system, the control unit configured to be separably connectable to a cartomizer of the vapor provision system which has a reservoir for holding aerosolizable substrate material, and the control unit comprising an aerosolizable substrate material detection system according to the second aspect and a power source configured to provide electrical power to the aerosolizable substrate material detection system and the cartomizer.

According to a fourth aspect of some embodiments described herein, there is provided a cartomizer for a vapor provision system, the cartomizer configured to be separably connectable to a control unit comprising a power source configured to provide electrical power to the cartomizer when the control unit and the cartomizer are connected, the cartomizer comprising a reservoir for holding aerosolizable substrate material, and an aerosolizable substrate material detection system according the second aspect.

According to a fifth aspect of some embodiments described herein, there is provided a method for detecting aerosolizable substrate material in a storage volume of a reservoir for a vapor provision system, comprising: using an optical source located externally of the reservoir to emit light into the storage volume; using an optical detector located externally of the reservoir to detect any light emitted by the optical source that has traversed an optical path through the storage volume to the optical detector; determining a characteristic of light detected by the optical detector; and deducing information regarding a depth of aerosolizable substrate material in the storage volume from the determined characteristic of the light.

These and further aspects of the certain embodiments are set out in the appended independent and dependent claims. It will be appreciated that features of the dependent claims may be combined with each other and features of the independent claims in combinations other than those explicitly set out in the claims. Furthermore, the approach described herein is not restricted to specific embodiments such as set out below, but includes and contemplates any appropriate combinations of features presented herein. For example, an aerosolizable substrate material detection system and method may be provided in accordance with approaches described herein which includes any one or more of the various features described below as appropriate.

BRIEF DESCRIPTION OF THE DRAWINGS

Various embodiments of the disclosure will now be described in detail by way of example only with reference to the following drawings in which.

DETAILED DESCRIPTION

Figure 1:
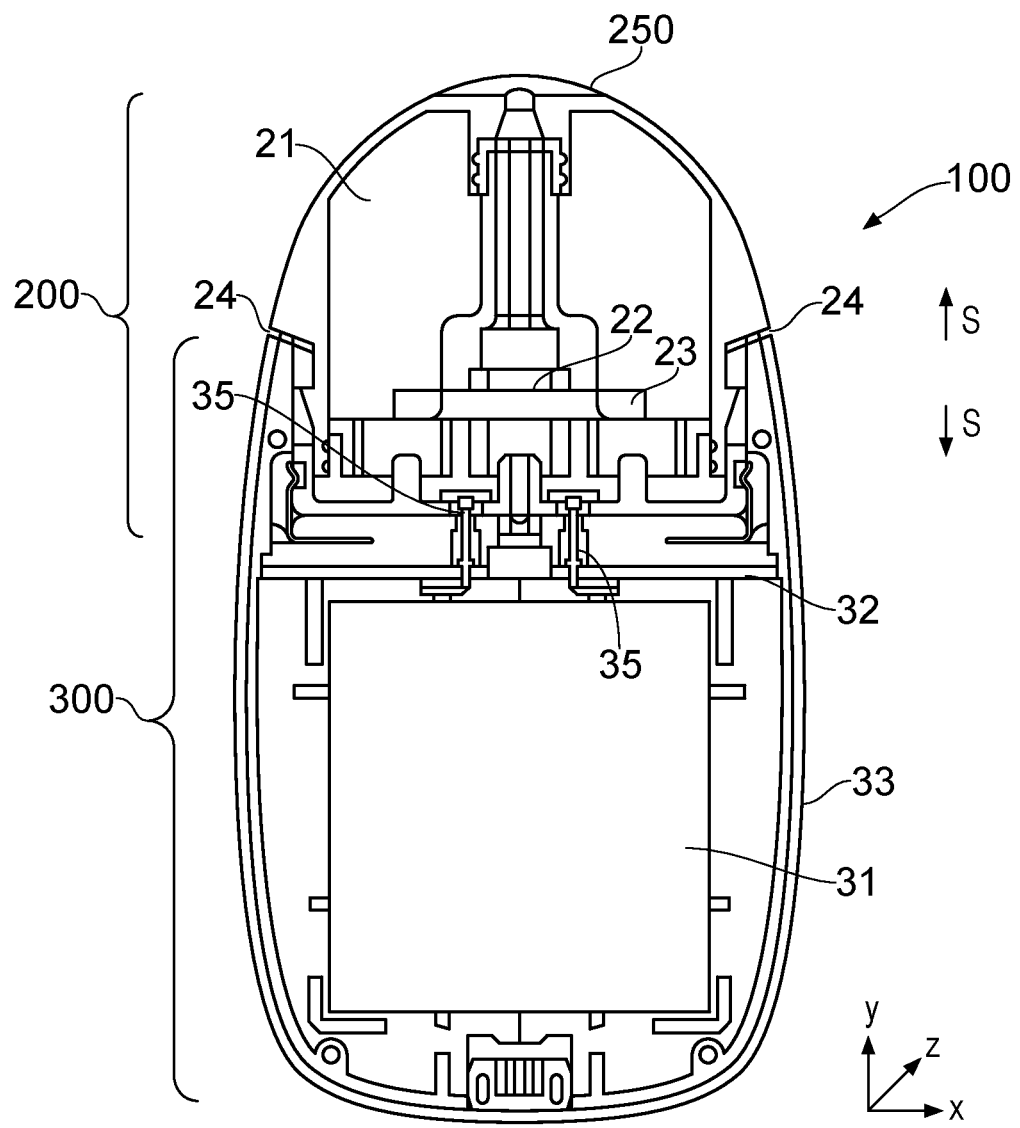
FIG. 1 shows a cross-section through an example e-cigarette comprising a cartomizer and a control unit in which examples may be implemented.

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to (but is not limited to) electronic aerosol or vapor provision systems, such as e-cigarettes. Throughout the following description the terms "e-cigarette" and "electronic cigarette" may sometimes be used; however, it will be appreciated these terms may be used interchangeably with aerosol (vapor) provision system or device. The disclosure is also applicable to hybrid devices and systems configured to deliver nicotine or other substances both by vaporizing aerosolizable substrate material such as a liquid and/or by heating a solid substrate such as tobacco or passing vapor through a solid substrate. The various terms noted above should be understood to include such devices. Similarly, "aerosol" may be used interchangeably with "vapor".

As used herein, the term "component" is used to refer to a part, section, unit, module, assembly or similar of an electronic cigarette that incorporates several smaller parts or elements, often within an exterior housing or wall. An electronic cigarette may be formed or built from one or more such components, and the components may be removably connectable to one another, or may be permanently joined together during manufacture to define the whole electronic cigarette.

Vapor provision systems can operate by generating vapor from a liquid, including by heating or by vibration. The liquid is stored in a reservoir or tank within the system, and a new supply of liquid is required when the reservoir becomes empty. Hence, the amount of liquid in the reservoir is of interest to the user, so that he has knowledge of how much the amount has been reduced by consumption, and when the reservoir will likely be empty, requiring replacement the whole system, or replacement or refilling of the reservoir. The present disclosure proposes to acquire information regarding the amount of liquid by use of an optical source to direct light into the interior of the reservoir and an optical detector to detect an amount of the light from the optical source which has been transmitted, reflected, scattered or otherwise modified by the contents of the reservoir. The amount of detectable light may depend on the amount, level or depth of liquid remaining in the reservoir, so a measurement of detected light can be used to deduce depletion of the liquid, to indicate to the user a remaining amount of liquid, or if the reservoir is empty or near-empty.

The proposed detection techniques are also applicable to vapor provision systems that produce vapor or aerosol by heating a substrate in gel form, rather than a conventional liquid. The gel material contains nicotine and/or other compounds such as flavorants which are released when the gel is heated, to provide a vapor for inhalation. The volume of gel becomes depleted by consumption of the vapor, in the same way a liquid, so detection of an amount of gel in a vapor provision device is of interest also. Liquids and gels comprising appropriate compounds can be considered as substrate materials from which an aerosol or vapor can be generated by heating or otherwise. Unless particularly stated, the present disclosure is to be understood as applying equally to both liquids and gels. Generic terms such as "aerosolizable substrate material", "aerosolizable substrate fluid" or "aerosolizable fluid" may be used to encompass both liquids and gels (and any similar materials). The present disclosure uses the term "liquid" extensively, but this is for simplicity only, and "liquid" should be understood to include gels and any other aerosolizable substrate materials unless stated otherwise. The aerosolizable substrate material, as a liquid or a gel, may be held in a reservoir in a "free-flowing" form, in that it is not absorbed into a matrix of absorbent material such as a sponge or wadding placed inside the reservoir.

FIG. 1 is a cross-sectional view through an example e-cigarette 100 to which a liquid detection system in accordance with examples of the present disclosure may be applied. The e-cigarette 100 comprises two main components, namely a cartomizer 200 and a control unit or power unit 300. The cartomizer 200 includes a chamber, tank or reservoir 21 containing a supply of liquid, a heater 22 generate vapor from the liquid, and a mouthpiece 250. The liquid in the reservoir 21 (sometimes referred to as e-liquid or source liquid) may include nicotine in an appropriate solvent, and may include further constituents, for example, to aid aerosol formation, and/or for additional flavoring. Nicotine may be absent from the liquid, in other examples. The cartomizer 200 further includes a wick 23 or similar facility to transport a small amount of liquid from the reservoir 21 to a heating location on or adjacent the heater 22. The combination of a wick and a heater may be referred to as an atomizer or vaporizer. The control unit 300 includes within a housing 33 a re-chargeable cell or battery 31 to provide power to the e-cigarette 100 and a printed circuit board 32 (PCB) for generally controlling the e-cigarette. When the heater 22 receives power from the battery 31, as controlled by the PCB 32, the heater 22 vaporizes the liquid from the wick 23 and this vapor is then inhaled by a user through the mouthpiece 250.

The cartomizer 200 and the control unit 300 are detachable from one another by separation in a direction along a longitudinal axis of the device, indicated in FIG. 1 by the arrows S, but are joined together (as in FIG. 1) when the device 100 is in use so as to provide mechanical and electrical connectivity between the cartomizer 200 and the control unit 300. Hence, the cartomizer and the control unit are separably connectable; they can be joined (coupled) together or separated apart according to user need. In this particular example, when the liquid in the reservoir 21 has been depleted, the cartomizer 200 is removed and a new cartomizer is attached to the control unit 300. Accordingly, the cartomizer 200 may sometimes be referred to as a disposable portion of the e-cigarette 100, while the control unit 300 represents a re-usable portion. Alternatively, the cartomizer may be configured so that the reservoir is refillable with liquid, and the cartomizer may or may not require detachment from the control unit for access to a filling port.

Figure 2:
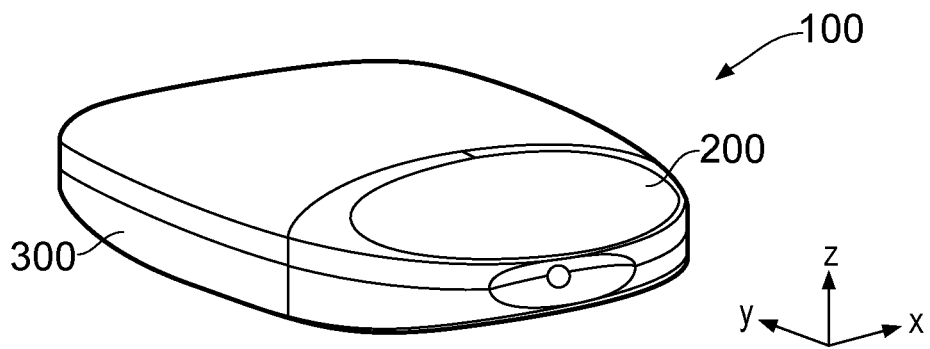
FIG. 2 shows a perspective view of the example e-cigarette of FIG. 1.

FIG. 2 is an external perspective view of the e-cigarette 100 of FIG. 1, in its assembled configuration with the cartomizer 200 coupled to the control unit 300 so that the e-cigarette is ready for use. The orientation is different from FIG. 1, as indicated by the xyz axes.

Figure 3:
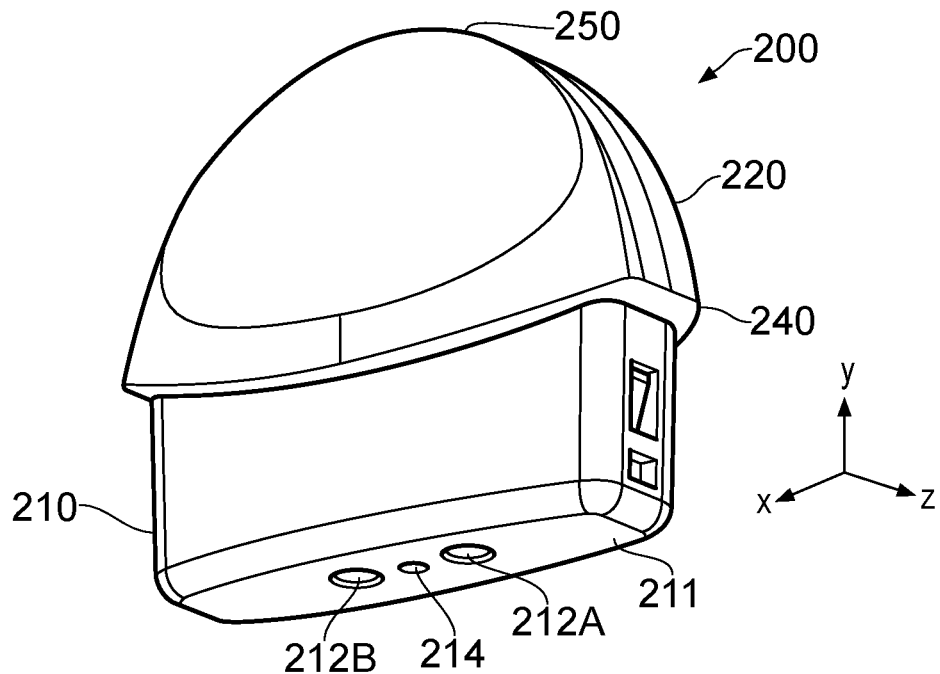
FIG. 3 shows a perspective view of the cartomizer of the example e-cigarette of FIG. 1.

FIG. 3 is a perspective external view of the cartomizer 200 of the e-cigarette of FIG. 1. The cartomizer 200 comprises two main portions (at least from an external viewpoint). In particular, there is a lower or base portion 210 and an upper portion 220. The upper portion 220 is shaped to provide the mouthpiece 250 of the e-cigarette. When the cartomizer 200 is assembled with the control unit 300, the base portion 210 of the cartomizer sits within the upper part of the housing 33 of the control unit 300, and hence is not externally visible, whereas the upper portion 220 of the cartomizer protrudes above the control unit 300, and hence is externally visible. Accordingly, the depth and width of the base portion 210 are smaller than the depth and width of the upper portion 220, to allow the base portion 210 to fit inside the control unit 300.

The base portion 210 has a lower face defined by a bottom wall 211. The bottom wall includes two larger holes 212A, 212B on either side of a smaller hole 214 which is for air inlet into the cartomizer interior. The larger holes 212A and 212B are used to accommodate positive and negative electrical connections from the control unit 300 to the cartomizer 200, provided by the conductive connectors 35 shown in FIG. 1. When a user inhales through the mouthpiece 250, the device 100 is activated and air flows into the cartomizer 200 through the air inlet hole 214 (via a pathway leading from ventilation slots 24 (see FIG. 1) defined at the juncture between the top edge of the control unit housing 33 and a lip 240 between the lower portion 210 and the upper portion 220 of the cartomizer 200). This incoming air flows past the heater (not visible in FIG. 3), which receives electrical power from the battery in the control unit 300 so as to vaporize liquid supplied from the reservoir 21 by the wick 23. This vaporized liquid is then incorporated or entrained into the airflow through the cartomizer, and hence is drawn out of the cartomizer 200 through the mouthpiece 250 for inhalation by the user.

Other features shown in FIGS. 1 to 3 are not described further here as not being relevant to the present disclosure.

Note also that the system shown in FIGS. 1 to 3 is purely by way of example, and the present disclosure is applicable to other shapes and configurations of vapor provision systems in which the various components are differently arranged. For example, the device may be unitary, and not separable into a cartomizer part and a control or power part. The reservoir may be separately replaceable or removable for refilling distinct from other components, perhaps provided in a cartridge format, or may be comprised within a cartomizer part together with a vapor generating element such as a heater for replacement together, as in the FIG. 1 arrangement. A cartomizer and a control unit might be arranged linearly as in FIG. 1, or in a side-by-side arrangement.

Figure 4:
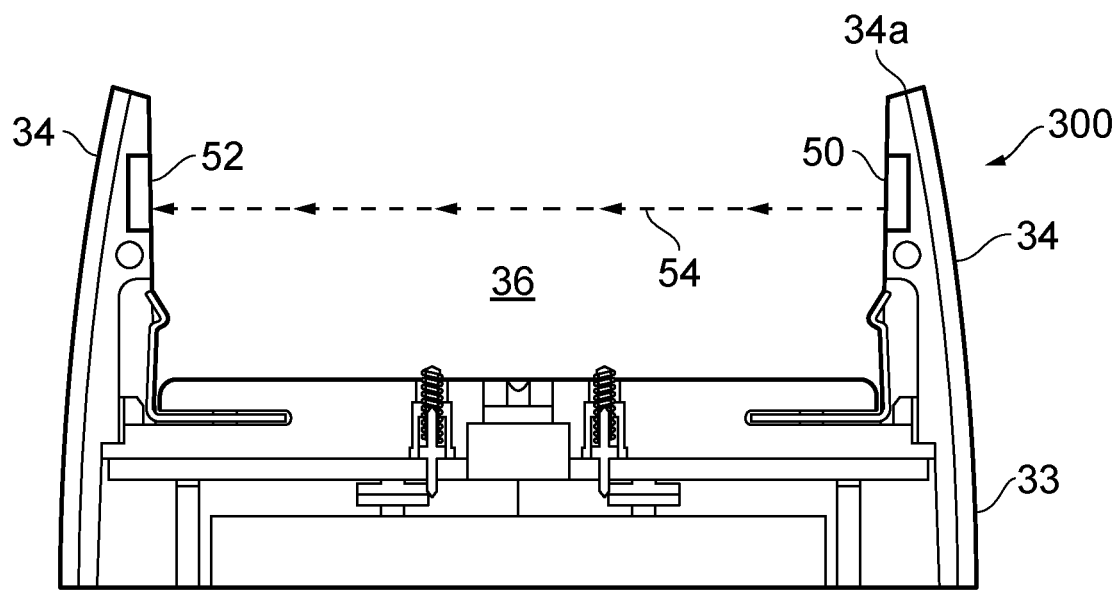
FIG. 4 shows a cross-sectional view of part of the control unit of the example e-cigarette of the FIG. 1, including components of an example liquid detection system.

FIG. 4 shows a cross-sectional side view of an upper part of the control unit 300 of the system of FIG. 1, separated from its cartomizer 200. As can be appreciated, the housing 33 of the control unit 300 includes an upstanding peripheral wall 34 at its upper part. This peripheral wall 34 surrounds and defines an open interior space or chamber 36 for receiving the lower portion 210 of the cartomizer 200 when the cartomizer 200 and the control unit 300 are connected together. When the units are connected, the peripheral wall 34 is located around the exterior of the lower portion 210, and its upper edge 34a is adjacent the lip 240 on the cartomizer 200. The lower portion 210 of the cartomizer includes a part of the reservoir 21 of the cartomizer, so that when the e-cigarette 100 is assembled, the reservoir is partly bordered by the peripheral wall 34. Hence the reservoir 21 is received in the interior space encompassed by the peripheral wall 34.

In accordance with an example of a liquid detection arrangement or system disclosed herein, the control unit 300 of FIG. 4 also comprises an optical source 50 (light source) configured to emit electromagnetic radiation (light) in the visible, ultraviolet or infrared parts of the electromagnetic spectrum. The optical source 50 is mounted on an interior surface of the peripheral wall 34 so as to be inwardly facing for emission of light 54 into the interior space 36. There is also an optical detector 52 configured to detect light at the wavelength or wavelengths emitted by the optical source 50, and positioned, also inwardly facing on the inner surface of the peripheral wall 34, to detect the light 54 emitted from the optical source 50 that has traversed the interior space 36. In this example, the optical source 50 and the detector 52 are arranged at the same height on opposite sides of the interior space 36, although in other examples, the source and detector can be differently positioned as will be described further below. Regardless of positioning, the source and detector are arranged so that a direct or indirect optical path for light from the source to the detector passes through the interior space 36.

When the cartomizer 200 is connected to the control unit 300, the reservoir is partially received in the interior space 36, and light 54 emitted from the optical source 50 is directed into the interior of the reservoir. The optical path from the source 50 to the detector 52 now passes through the interior liquid storage space of the reservoir, so that emitted light is incident on the reservoir contents and may be transmitted through the contents. After travelling the optical path through the contents of the reservoir (which may be full of liquid, partially full of liquid, or empty of liquid), the light 54 is incident on the detector 52 where it is detected for measurement. Note that the source 50 and the detector 52 are recessed into the inner surface of the peripheral wall 34 in this example so as not to interfere with the close fit of the cartomizer lower portion 210 inside the peripheral wall 34.

The reservoir 21 is formed with a wall or walls (corresponding in this example device to all or part of the walls forming the lower portion 210 of the cartomizer 200) which are at least partially transparent to the wavelength or wavelengths of light emitted by the optical source 50, to allow the light to enter the interior of the reservoir after emission, and to exit the interior of the reservoir for detection. The transparency can be achieved by forming the walls of the reservoir from a material that is transparent or transmissive at the appropriate wavelength(s), or by providing windows in the walls of the reservoir which are aligned with the source 50 and the detector 52 and formed from a material with the appropriate transparency/transmissivity. The transparency or transmissivity of the material may be approximately 100% at the wavelength(s) of interest, or may be less than 100% so long as there is a level of light remaining which is detectable by the detector 50 after a first passage through the reservoir wall from the source 50 into the interior of the reservoir and a second passage through the reservoir wall from the interior to the detector 52. This optical transmission of the reservoir walls may be calculated with regard to the thickness of the material used, since an increased thickness of material will absorb a greater amount of incident light.

The arrangement, and other examples of an optical source and corresponding optical detector located externally of a reservoir, enables the detection of liquid held in the reservoir. The presence of liquid along a direct or indirect optical path between the optical source and the optical detector that at least partially traverses the reservoir's interior storage volume can affect, modify or induce a characteristic, parameter or property of light propagating along that optical path. Hence, light arriving at the detector has at least one characteristic arising from its propagation through the reservoir, and measurement or analysis of this detected light will allow the characteristic to be measured, monitored, identified or detected. The value (a relative value or a "binary" value) of the characteristic can then be used to deduce the presence or absence of light along the optical path. In simple arrangements, the presence or absence of the characteristic or a change in the characteristic may be detected as a simple "binary" result indicating whether or not there is any change, and then used to infer whether or not there is liquid along the optical path that has produced the characteristic or the change in characteristic. The absence of liquid will produce no change in the characteristic, and the presence of liquid will give rise to the change. Alternatively, the absence of liquid will not produce the characteristic and the presence of liquid will produce it. In more complex arrangements, the characteristic may show a measurable variable value or change in value according to the quantity of liquid through which the light has passed or the position of the liquid surface in the reservoir. This may be used to determine a level or depth of liquid which is or is not present along the optical path, since the characteristic is modified in proportion to the amount of liquid. Hence, the amount of liquid in the reservoir may be measured or estimated, as opposed to a simple result that liquid is or is not present. The height or depth of the source and the detector relative to the depth of the reservoir (when held in a predetermined orientation, such as an upright, vertical, position with the mouthpiece pointing upwards) can be chosen in some examples to detect or identify when the depth or level of liquid in the reservoir is below a predetermined depth, when, for example, there will be no liquid along the optical path and hence no change in the characteristic induced in the propagating light. In some cases, the chosen depth may be low in the reservoir so that a depth of liquid below this chosen depth indicates that the reservoir can be considered to be empty or near-empty. This information can be communicated to the user to inform him that the reservoir should be replaced or refilled to provide fresh source liquid for vaporization.

Figure 5A:
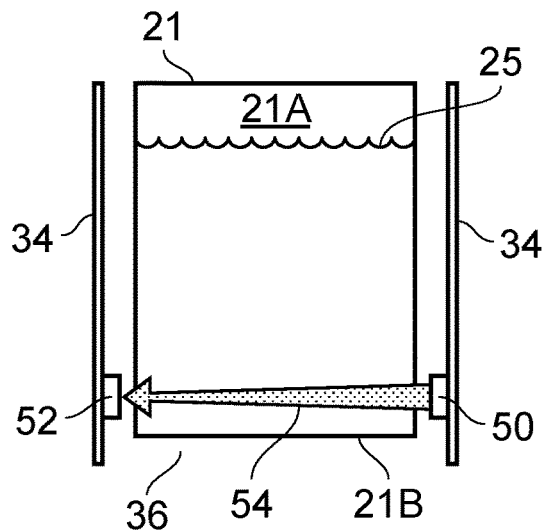
FIGS. 5A and 5B show schematic longitudinal cross-sectional views of a first example liquid detection system in use with a full reservoir and an empty reservoir.
Figure 5B:
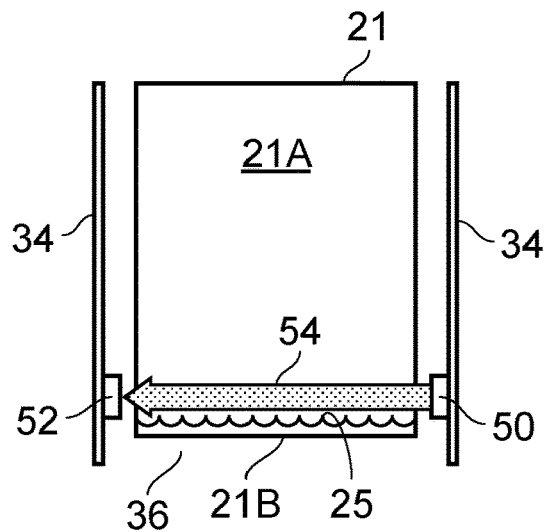

FIGS. 5A and 5B show a simplified schematic cross-sectional view of components of an e-cigarette provided with a liquid detection system such as the FIG. 4 example. A reservoir 21 comprises a wall that defines an interior storage volume 21A of the reservoir 21 for holding source liquid 25. The source liquid is held as freely flowing liquid, and is not absorbed in any wadding or other matrix material inside the reservoir. In reality the reservoir 21 will comprise one or more outlets for supplying liquid to a wick or other liquid transport means for delivery to a vapor generator, but for simplicity this is not shown in FIGS. 5A and 5B. The reservoir 21 is located in a space 36 defined by one or more boundary walls 34. An optical source 50 and an optical detector 52 are mounted on inside surfaces of the boundary walls 34, facing inwardly into the space 36. An optical source 50 and an optical detector 52 are oppositely arranged across the space 36 so that the reservoir 21 is interposed between the source 50 and the detector 52 when it is received in the space 36. The optical path from the source 50 to the detector 52 thus passes through the storage volume 21A. The source 50 and the detector 52 are positioned adjacent a lower part of the reservoir 21, near a base wall 21B of the reservoir 21. These orientations assume a vertical axis for the reservoir 21 which is in the vertical direction of the Figures, in the plane of the page. This vertical axis can be defined as the vertical axis of the reservoir 21 when the e-cigarette in which it is comprised is held with its mouthpiece pointing upwards or near-upwards. In this orientation the liquid 25 in the reservoir 21 will flow downwards towards the base wall 21B. The reservoir 21 can be considered to have a depth in this vertical direction. The source 50 and the detector 52 are positioned at a depth or depths (source depth and detector depth) relative to the reservoir depth. Also, liquid 25 held in the reservoir 21 has an amount, depth or level indicated by the depth of the liquid surface relative to the reservoir's depth dimension when the e-cigarette is held vertically. In the depicted example of FIGS. 5A and 5B, the source 50 and the detector 52 are arranged at the same depth relative to the reservoir, facing each other on opposite sides of the reservoir. The optical path is hence orthogonal to the reservoir depth direction. Accordingly, when the source 50 emits light 54, the light travels towards the reservoir 21, passes through the material of the reservoir wall, enters the interior 21A of the reservoir 21, traverses the interior until it reaches the opposite wall, passes through the material of the opposite wall, and is incident on the detector 52.

This configuration enables liquid detection to return a simple result indicating whether or not there is liquid above the source depth and detector depth. Because the source and detector are proximate the base wall 21B, a detected liquid level above this depth is interpreted as the reservoir containing usable source liquid (it is not empty), and a failure to detect liquid above this depth is interpreted as the reservoir being empty of usable source liquid.

FIG. 5A shows the reservoir 21 nearly full of source liquid 25. The level or depth of the liquid is defined by an upper surface which is near the top of the reservoir (in its vertical orientation). The lower part of the reservoir interior 21A is hence filled with liquid 25, including the part through which the optical path passes. Light 54 emitted from the source 50 therefore passes into the liquid as it traverses the interior of the reservoir on its path to the detector 52. If the wavelength of the light and the optical absorption properties of the source liquid are chosen so that there is an appreciable level of optical absorption of the light by the amount of liquid comprised in the optical path between the source 50 and the detector 52, the amount of light that reaches the detector 52 will be measurably less than the amount emitted from the source 50. This is represented in FIG. 5A by the decreasing width of the arrow representing the light 54. This reduced amount of light at the detector 52 compared to the amount of emitted light indicates the presence of liquid along the optical path, and hence in the reservoir. From this measurement, it can be deduced that the reservoir is not empty, and liquid is available for vapor generation. By an "appreciable level of optical absorption", it is meant that the liquid provides enough absorption to decrease the light intensity by an amount which is outside an amount that might be attributable to noise at the detector or measurement error. For example, a minimum of 5% absorption, giving a detected measurement of about 95% of the emitted light level (ignoring absorption in the reservoir walls) might be acceptable. However, a larger absorption may give a clearer result, such as absorption in a range of 10% to 90%, to give a detected light level when liquid is present of 90% to 10% of the emitted light. Moreover, the liquid may absorb substantially all the light emitted from the source 50, so that no light is detected at the detector 52. However, this arrangement prevents the detection of liquid in the reservoir from being distinguishable from an operational failure in the source or the detector, either of which could also give a zero light detection result. Hence, a less than total absorption of the light by the liquid may be preferred.

Accordingly, if there is a depth of liquid in the reservoir which greater than the depth of the source and detector with respect to the reservoir, the liquid absorbs at least some of the light from the source and the amount of detected light is lower than the amount of emitted light. This result is interpreted as liquid being present in the reservoir, or the reservoir is not empty FIG. 5B shows the reservoir 21 when it is virtually empty, so that the liquid 25 is below the source and detector depths. Accordingly, light 54 emitted by the source 50 follows the optical path to traverse the reservoir storage volume 21A without experiencing any absorption by liquid, and the intensity of the light 54 reaching the detector 52 is substantially equal to the emitted light intensity (ignoring any absorption by the reservoir walls). Hence, the arrow representing the light 54 in FIG. 5B has a constant width, to indicate a constant intensity. This undiminished light level is measured by the detector 52, indicates that any liquid in the reservoir is below the depth of the optical path, and is interpreted as the reservoir being empty.

In this example, the characteristic of the light detectable at the detector from which the liquid level in the reservoir may be deduced is the amount, level or intensity of the light, in particular compared to the amount of light emitted by the source. A first amount of detected light, corresponding to no absorption by liquid and being substantially equal to the amount of emitted light, indicates an empty reservoir, while a second amount of detected light which is less than the first amount and arises from absorption of the light by liquid along the optical path, indicates a non-empty reservoir.

The example configuration of FIGS. 5A and 5B can be modified by placing the source and the detector at a different detection depth compared to the reservoir. For any detection depth, a detected first amount of light indicates that the liquid level is less than the detection depth, and detected second amount of light smaller than the first amount indicates that the liquid level is above the detection depth, so that there is optical absorption by the liquid along the optical path. Therefore, a paired source and detector might be positioned at or near a depth which is half the depth of the reservoir to detect when the liquid level falls below the reservoir being half-full, or at any other detection depth to detect other proportions of liquid in the reservoir.

Figure 6:
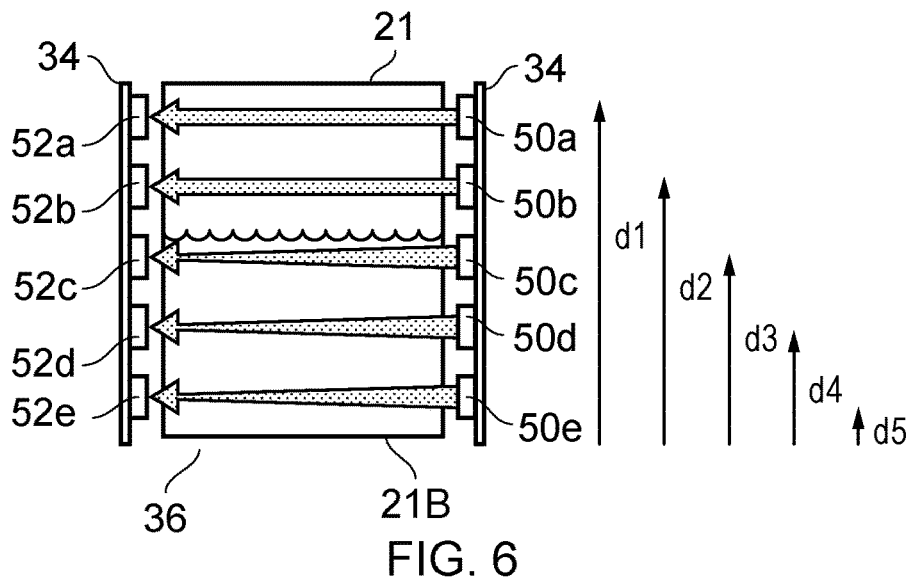
FIG. 6 shows a schematic longitudinal cross-sectional view of another example liquid detection system.

FIG. 6 shows an example configuration that extends this concept so that multiple different liquid depths can be detected. A reservoir 21 is received in a space 36 between walls 34 as in the FIGS. 5A and 5B examples, but in this example each of a plurality of optical sources 50a to 50e is paired with one of a plurality of optical detectors 52a to 52e, each pair arranged at the same detection depth relative to the reservoir so as to provide a plurality of detection depths d1 . . . dn, in this example d5 since there are five source-detector pairs. If light 54 is emitted from each source 50a to 50e (simultaneously or sequentially), there will be a corresponding amount of light detected at each detector 52a to 52e, where the amount of light detected depends on whether there is liquid present in the optical path for a particular source-detector pair. A detector which receives a first amount of light corresponding to no optical absorption by source liquid can be deduced to be above a level of liquid in the reservoir. A detector which receives a second amount of light less than the first amount by an amount corresponding to optical absorption by liquid along the optical path can be deduced to be below a level of liquid in the reservoir. Hence, the depth of liquid in the reservoir can be deduced to be not less than the depth of the highest detector (from the reservoir base wall 21B) which measures a second, reduced amount of light. In the depicted example, the liquid 25 has a depth such that the two higher source and detector pairs 50a-52a and 50b-52b have optical paths unimpeded by liquid; the liquid depth is lower than both the depth d1 of the highest detector 52a and the depth d2 of the second detector 52b. These detectors measure a first amount of light 54. The liquid level is above the depth d3 of the third source and detector pair 5ac-52c, however, so that all of the third, fourth and fifth (lowest) detectors all detect a second, smaller, amount of light 54 owing to absorption of light by the liquid. Hence, the detection system returns the result that the liquid has a depth which is at least d3, the depth of the third source and detector pair 50c-52c, and/or is less than d2, the greater depth of the second source and detector pair 50b-52b. As the liquid is consumed, the depth of liquid decreases, and the third source and detector pair 50c-52c will register a first, higher amount of light, indicating that the liquid has a depth which is at least d4 and/or is less than d3. Then the fourth source and detector pair 50d-52d will register a first, higher amount of light, indicating that the liquid has a depth which is at least d5 an/or is less than d4. Finally, the fifth source and detector pair 50e-52e will register a first, higher amount of detected light, from which it is deduced that the liquid has a depth less than d5, which, since this depth is small and close to the base wall 21B, can be considered, if desired, to correspond to an empty reservoir. Hence, circuitry or a processor configured to receive and process the output from the detectors and make a deduction regarding liquid level therefrom, can look at the output from every detector, identify the highest source/detector pair which has a reduced optical signal and/or the lowest source/detector pair which has an undiminished optical signal, and output a deduction that the liquid depth corresponds to (or is not less than or not greater than) the depth of the identified source-detector pair.

The FIG. 6 example can be extended to include more source and detector pairs more closely spaced in the depth direction to provide a higher resolution of liquid detection results, in that a larger number of liquid depths can be distinguished one from another. Also, the array of discrete optical sources may be replaced by a single elongate optical source arranged vertically so as to span all or some of the reservoir depth and direct light onto the plurality of detectors on the other side of the reservoir. The measurement resolution in the depth direction is provided by the discrete nature of the detectors. Additionally or alternatively, the array of discrete detectors might be replaced by a single elongate optical detector with the capability to resolve or distinguish different positions for incident light. The detector surface can be divided up and the measurements at each position used to mimic or correspond to the separate responses from an array of discrete detectors.

The characteristic of a reduced amount of light as an indicator of the presence of liquid along the optical path can be used in a more sophisticated arrangement which is able to obtain an indication of the actual depth of the liquid in a reservoir (as opposed to deducing a mere presence or absence of liquid) from a single source and detector pair.

Figure 7:
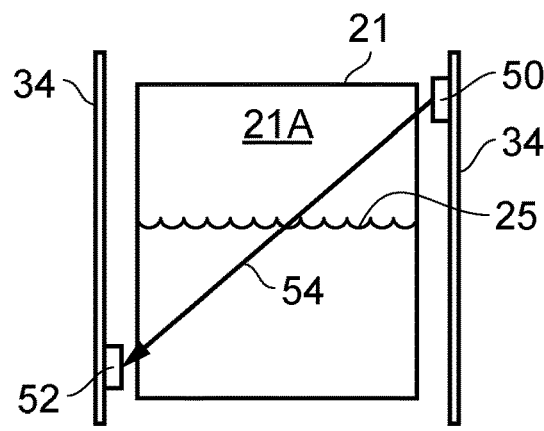
FIG. 7 shows a schematic longitudinal cross-sectional view of a further example liquid detection system.

FIG. 7 shows a schematic cross-sectional view of an example liquid detection system configured in this way. In contrast to the foregoing examples in which an optical source is paired with an optical detector arranged at the same height or depth relative to the reservoir in its vertical orientation, an optical source is arranged at a first depth and an optical detector is arranged at a second depth different from the first depth. As depicted, the optical source 50 and the optical detector 52 are mounted on the surrounding side walls 34 facing inwardly into opposite sides of the reservoir as before, but the optical source 50 is positioned near or level with the top of the reservoir 21 and the optical detector 52 is positioned near or level with the base of the reservoir 21. The optical path of light 54 emitted from the source 50 to reach the detector 52 thus extends over much of the depth of the reservoir, rather than being orthogonal to the depth as in the FIGS. 5A, 5B and 6 examples. Light is able to traverse the interior storage volume 21A of the reservoir 21 from top to bottom, along an optical path which in this example is at an angle to the vertical direction.

This orientation of the optical path means that when the reservoir is held vertically, any liquid 25 in the reservoir 21 will intercept the optical path so that absorption occurs and the amount of light 54 received at the detector is reduced compared to the amount of light emitted from the light source 50. The proportion of the optical path which passes through the liquid 25, and hence the degree of optical absorption which takes place, depends on the depth of liquid 25 in the reservoir 21, however. If the reservoir 21 is full or nearly full, all or most of the optical path will lie through the liquid 25 and a lot of absorption will occur. The optical intensity will be significantly reduced so that only a small amount of light 54 is received at the detector 52. If the reservoir 21 is becoming empty, the depth of liquid 25 is low and most of the optical path will pass through the empty reservoir space 21A with only a small proportion of it passing through the liquid 25. A lesser amount of absorption takes place, and a larger amount of light is received at the detector 52. If the reservoir 21 is completely empty, or the liquid level is below the detector depth, there will be no liquid in the optical path to produce absorption, and the amount of detected light will be undiminished compared to the emitted level (ignoring any absorption in the reservoir walls).

Thus, the magnitude of the light signal (intensity) detected at the detector varies with the depth of liquid 25 in the reservoir 21, with a large depth of liquid giving a small light signal and a shallow depth of liquid giving a large light signal. Assuming a linear absorption response of the liquid to the incident light, the relationship is a linearly proportional relationship, and the level of liquid can be readily determined from the measured light amount, subject to calibration of the system to determine the expected detectable amount of light for a full reservoir and an empty reservoir, or more generally to an optical path completely in liquid and an optical path completely out of liquid. Note that these two extremes correspond to the smaller second amount of detected light and the larger first amount of detected light in the FIGS. 5A, 5B and 6 examples.

Figure 8:
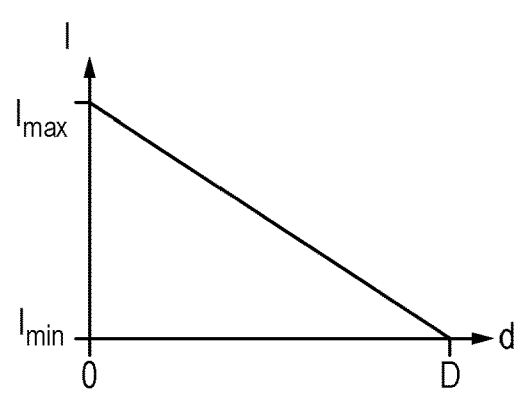
FIG. 8 shows a graph of an example response of the liquid detection system of FIG. 7.

FIG. 8 shows a simple plot of the relationship between detected light level or intensity I and liquid depth d. As mentioned, the relationship is linear, with an inverse proportionality. An empty reservoir or reservoir with liquid below the level of the detector has a liquid depth d=0, producing a maximum amount of detectable light $I_{max}$ owing to zero absorption. A full reservoir with liquid depth d=D encompassing the full length of the optical path produces a minimum amount of detectable light $I_{min}$ owing to maximum absorption. Between these extremes, the light intensity decreases linearly with increasing depth of liquid.

Accordingly, the circuitry or processor controlling the liquid detection system can readily determine the depth of liquid from a measurement of detected light intensity by simple calculation using an equation describing a relationship such as that depicted in FIG. 8, or by consulting a stored look-up table that maps values of detected light intensity to liquid depth previously calculated from the linear relationship or determined from measurements.

This calculated value of liquid depth might be communicated to the user as a direct numerical value of the liquid depth, or as an approximate percentage of the total reservoir capacity to give a general indication of liquid consumption and the remaining amount of liquid, or simply as an indication that the reservoir is "full" if the detected liquid depth exceeds a preset threshold value or "empty" is the detected liquid depth is below the preset threshold.

While FIG. 7 shows the liquid detection system arranged with the optical source 50 located at or towards the top of the reservoir and the optical detector 52 arranged at or towards the bottom of the reservoir, this configuration can be reversed so that the detector is at or near the top and the source is at or near the bottom.

The positions of the source and detector in the FIG. 7 example, on the walls 34 surrounding the sides of the reservoir, are convenient for a electronic cigarette configured for insertion and removal of the reservoir along an axis substantially parallel to the vertical or depth axis of the reservoir, as in the example device of FIGS. 1 to 4. In other configurations, the source and/or the detector may be differently positioned, for example, above and below the reservoir.

Figure 9:
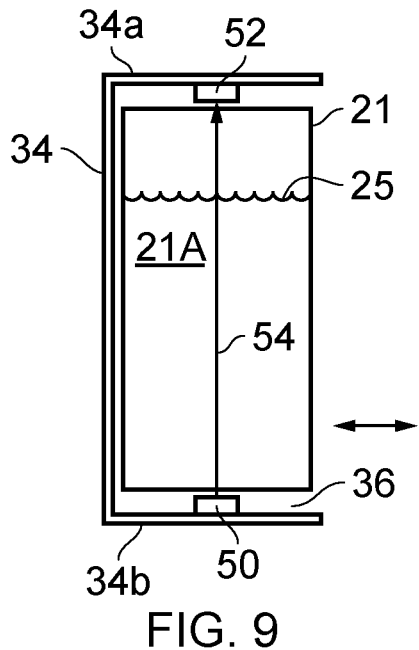
FIG. 9 shows a schematic longitudinal cross-sectional view of a still further example liquid detection system.

FIG. 9 shows a simplified cross-sectional view of an example liquid detection system configured in this way. In this example, the walls that define the space 36 for receiving the reservoir 21 comprise a side wall 34, an upper wall 34a and a lower wall 34b. An open side opposite the side wall 34 allows a reservoir to be inserted and/or removed in a direction substantially orthogonal to its vertical depth, indicated by the double-ended arrow. Once installed in the space 36, the surrounding upper wall 34a lies above the top of the reservoir 21 and the lower wall 34b lies under the base wall 21B of the reservoir 21. The optical source 50 is mounted on the lower wall 34b to direct emitted light 54 substantially vertically upwards into the interior of the reservoir 21. The optical detector 52 is mounted on the upper wall 34a facing downwardly towards the reservoir 21 and the detector 50, to receive the emitted light 54 after it has traversed the storage volume 21A of the reservoir 21. The optical path is therefore substantially vertical or near-vertical, and traverses the full depth of the reservoir. An arrangement such as this can detect and distinguish every depth of liquid from a completely full reservoir to a completely empty reservoir. Otherwise, the deduction of the liquid depth can be the same as that described for FIG. 7, using a relationship between liquid depth and detected light amount such as that in FIG. 8. Either of the source 50 and/or the detector 52 may be displaced in a sideways direction to change the optical path to a sloped path making an angle to the vertical axis if convenient. Also, the positions of the source and the detector may be reversed, so that the source is above the reservoir and the detector is below the reservoir.

Light incident on and travelling through a liquid (or other medium) will experience other interactions in addition to linear optical absorption reducing the intensity of light travelling along a straight-through path. These other interactions include scattering. Accordingly, in other examples it is proposed to deduce the presence of liquid by detecting light scattered by the liquid. The characteristic of the detected light which is employed by the light detection system is again the amount, level, amplitude or intensity of the detected light, but it is the amount arising from scattering which is detected rather than the amount remaining after any absorption. Optical scattering is a physical process by which light is forced to deviate from its otherwise straight path through a medium by localized non-uniformities (scattering centers) in the medium such as particles, bubbles, and density fluctuations. Overall, the presence of a liquid along the optical path will cause at least some scattering so that some light will deviate from a straight path and be directed elsewhere by one or more scattering events within the liquid. If this scattered light can be detected, its existence shows the presence of the liquid. If no scattered light is detected, it can be concluded that no liquid is present along the expected straight-line, or direct, optical path. In the context of liquid detection in a reservoir, one or more detectors can be positioned at locations around a reservoir which are spatially separated from the position for detecting light on a direct optical path for light emitted into the reservoir from an optical source. If these detectors receive and detect light, one can deduce that liquid is present in the reservoir, causing light to be scattered onto these detectors. If the detectors receive no light so that no output signal representing detected light is produced, one can deduce that the reservoir is empty, or at least that any liquid present is below a depth at which the optical source introduces light into the reservoir.

Figure 10:
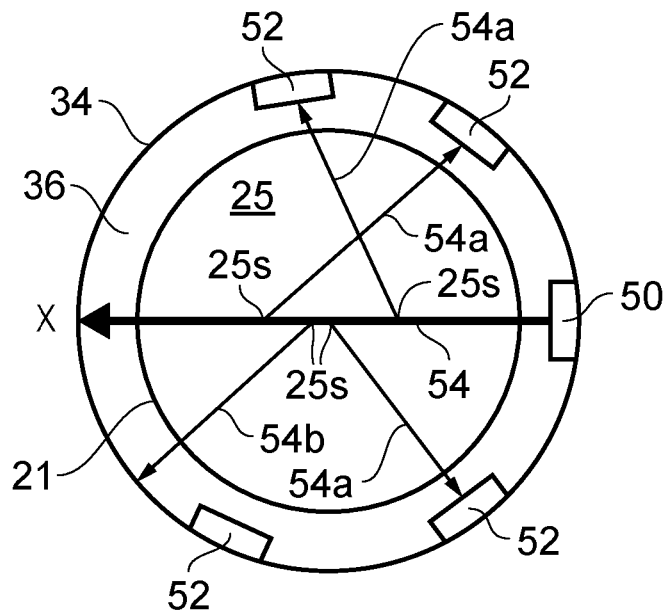
FIG. 10 shows a schematic transverse cross-sectional view of another example liquid detection system.

FIG. 10 shows a simplified schematic cross-sectional view transverse view of a reservoir with accompanying liquid detection system according to a further example that utilizes optical scattering. The cross-section is orthogonal to the vertical depth of the reservoir. A surrounding wall 34 defines a space or chamber 36 for receiving a reservoir 21 for holding liquid. An optical source 50 is mounted on the inner surface of the wall 34, facing inwardly so as to be able to direct its emitted light output into the interior of the reservoir 21, where liquid 25 is currently stored. One or more, in this example, four, optical detectors 52 are mounted on the inner surface of the wall 34 for receiving light travelling outwardly from the reservoir interior. The detectors are spaced apart around the defined space 36 at various angular separations from the optical source 50.

Much of the light 54 emitted from the optical source will traverse the reservoir interior along a straight and direct optical path to a point X opposite the source 50. In this example, there is no detector located to receive this straight-through light. Some of the light passing through the reservoir will undergo scattering at any scattering centers 25s on which it is incident, and be directed away from the direct optical path, at any angle depending on the nature of the scattering event, and onto an indirect optical path. Multiple scattering events will typically occur over the length of the direct optical path so that scattered light will be directed in many directions. Some scattered light 54b will simply exit the reservoir through the reservoir wall and be incident on the surrounding wall 34. Other scattered light 54a will take a path through and out of the reservoir that is aligned with a detector 52, however, and will be detected. Therefore, the system is configured to deduce that if light emitted from the source 50 is received at one or more detectors 52, liquid is present in the reservoir 21 and causing scattering of the emitted light. If no detectors detect any light, scattering is absent and it is deduced that the reservoir contains no liquid, or contains liquid only at a level below the lowest reservoir depth through which the direct optical path passes. The optical source may be arranged at or near the base of the reservoir so that a null result (no detected scattered light) more accurately corresponds to an empty or near-empty reservoir. The actual amount of light at any detector is not significant; the detection of light per se is sufficient to identify scattering that indicates the presence of liquid. However, a detection threshold might be included in the assessment of the detector outputs, where levels of detected light below the threshold are disregarded. This can exclude potential false positive results owing to noise or error at a detector or the detection of ambient or other light that has not arisen from scattering in liquid.

Note that in FIG. 10, single scattering events are shown for simplicity. In reality, light may undergo multiple scattering events before exiting the reservoir so that the indirect optical path from source to detector may comprise multiple angular deviations. Also, the detectors need not be positioned at the same depth relative to the reservoir as the optical source. Scattering occurs in three dimensions so an indirect optical path to a detector can occupy other depths within the reservoir. More or fewer than four detectors, arranged at the same or different depths, can be provided as preferred. If the liquid is formulated to generate a high degree of scattering, a small number of detectors (including just one detector) may be sufficient to ensure that any scattering arising is detected, particularly if the detectors have high sensitivity. For a liquid with fewer scattering centers, more detectors may be preferred. Alternatively, one or more large area detectors can be used to cover a wider range of scattering angles to ensure that scattered light is captured.

While the FIG. 10 example lacks a detector at the position X to detect light from the direct optical path from the source 50, a detector may be included here, so long as its output is disregarded from the analysis that determines if any scattered light has been detected (indicating the presence of liquid in the reservoir). It may be useful for checking that the optical source is operational and emitting the required light, or for calibrating the output of the optical source, for example.

As an alternative to optical absorption and optical scattering, examples of liquid detection systems may be configured to deduce the presence of liquid by detecting light which has been reflected from the air-liquid interface at the liquid surface. The position of the liquid surface, dependent on the liquid depth, can alter a characteristic of the reflected light which can be determined from the response of the optical detector and used to determine the depth of the liquid, or in simple arrangements, the presence or absence of liquid.

Figure 11:
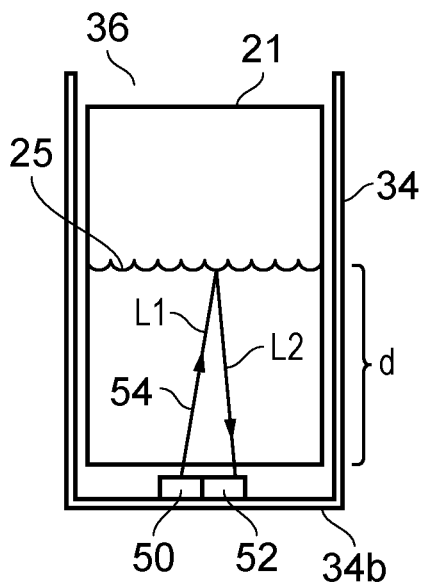
FIG. 11 shows a longitudinal cross-sectional view of a yet further example liquid detection system.

FIG. 11 shows a simplified schematic cross-sectional side view of a first example system that utilizes light reflection. A surrounding wall 34 defines a space 36 for receiving a reservoir 21 for holding liquid 25. The surrounding wall 34 includes a lower wall 34b that lies underneath the base of the reservoir 21. An optical source 50 and an optical detector 52 are mounted on the inner surface of the lower wall 34b, facing inwardly into the space 36 so that the optical source 50 can emit a beam of light 54 into the interior storage volume of the reservoir and the detector 52 can detect light returned from the interior storage volume.

In use, the source emits light 54 into the reservoir 21 when the reservoir 21 is held in a vertical orientation so that any liquid therein is in the lower part of the storage volume. The light 54 propagates along a linear optical path through the liquid 25 to the liquid surface. Some of the light will pass through the interface between the liquid 25 and air in the space above the liquid in the upper part of the storage volume. A proportion of the light will be reflected at the interface, however, and will propagate through the liquid 25 back towards the base of the reservoir 21 to be collected by the optical detector 52. The reflection therefore creates an optical path between the source 50 and the detector 52 that extends from the source 50 to the liquid surface and from the liquid surface to the detector 52. This optical path has a length L equal to the distance $L_1$ from the source 50 to the surface plus the distance L2 from the surface to the detector 52. If the source 50 and the detector 52 are very closely spaced so as to be spatially coincident or near-coincident, and the source is arranged to direct the light beam substantially parallel to the vertical depth axis of the reservoir (which is beneficial since the reflected light will not be angularly displaced), $L_1$ and $L_2$ will be substantially equal and also equal to the liquid depth d, and $L=L_1+L_2$ or $L=2L_1=2d$. Note that in FIG. 11 the source 50 and detector 52 are shown as non-coincident, and the light path slightly non-vertical, for clarity.

It will be appreciated that $L_1$ and $L_2$, and hence the total path length L, will vary with the depth of liquid 25 in the reservoir 21. If the reservoir 21 is full or nearly full, the liquid surface will be towards the top of the reservoir, and the path length to the surface and back from the base of the reservoir will be relatively long. If the reservoir is less full, the liquid surface will be closer to the base of the reservoir, and the path length to the surface and back will be relatively short. The propagation speed of light in a given medium is constant, so the time for light to propagate from the source to the detector will vary with the liquid depth, as the path length to and from the surface varies. Accordingly, the present example proposes to deduce liquid depth by measuring the propagation time or "time of flight" for a pulse of light to travel the optical path from source to detector via the liquid surface.

The speed of light v in the source liquid is a known property of the liquid. The time of flight t for light to traverse the optical path is t=L/v. Therefore, the control circuitry or processor is configured to cause the source 50 to emit a short pulse of light 54 at a time $t_1$, and to measure the time t which elapses until the returning reflected light is detected at the detector 52 at a later time $t_2$, where $t=t_2-t_1$. The processor is then able to calculate the path length L using the known speed v and the measured time t according to the formula noted above, and estimate the liquid depth by halving this value, since L=2d or d=L/2 as noted above. This calculated value of liquid depth might be communicated to the user as a direct numerical value of the liquid depth, or as an approximate percentage of the total reservoir capacity to give a general indication of liquid consumption and the remaining amount of liquid, or simply as an indication that the reservoir is "full" if the detected liquid depth exceeds a preset threshold value or "empty" is the detected liquid depth is below the preset threshold. Also, since the speed v is constant, the depth is directly proportional to the measured time, so it is possible to avoid the intermediate calculation including speed. The system may be calibrated for a liquid or liquids with a given speed of light, to derive a relationship between depth and time from which the liquid depth can be deduced by calculation. Alternatively, a set of values can be stored as a look-up table from which a depth value can be extracted for a measured time. In a simple embodiment, a threshold value of time can be set that corresponds to a minimum depth of fluid below which the reservoir is considered to be empty. Measured times of flight in excess of the time threshold value indicate a liquid depth greater than the predetermined minimum so an indication of a "full" reservoir can be reported from the system, and a measured time of flight shorter than the threshold indicates a low liquid level that can be reported as an "empty" reservoir.

Figure 12:
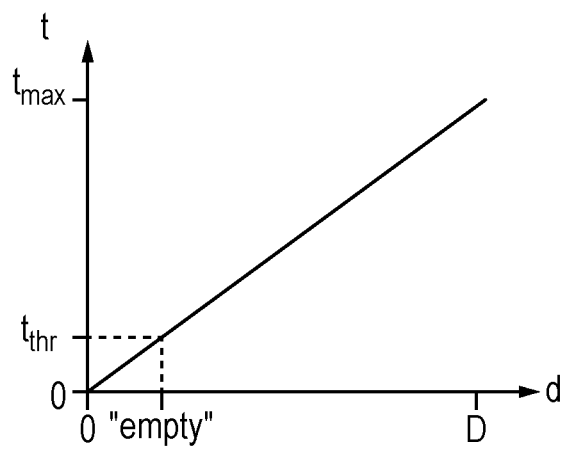
FIG. 12 shows a graph of an example response of the liquid detection system of FIG. 11.

FIG. 12 shows an example graph of a possible relationship between measured time of flight t and liquid depth d. The relationship is proportional and linear, and for a full reservoir with a liquid depth D there is a maximum measurable time of flight $t_{max}$, being the time taken for the light to propagate from the reservoir base to the top and back to the base, i.e. twice the full depth of the reservoir storage volume. When the reservoir is empty, the liquid depth is zero and there is no liquid surface to cause a reflection, so no light is returned to the detector and no time of flight can be measured, corresponding to a zero flight time. It may be beneficial to provide a low reflective or non-reflective surface for the inside of the top wall of the reservoir to reduce or prevent reflection of light back to the detector in the absence of any liquid. If desired, a shallow liquid depth below which the reservoir is considered to be "empty" can be set, with a corresponding time of flight $t_{thr}$, so that measured times below this threshold are reported as an empty tank.

According to this example, the characteristic of the light which is induced by the presence or absence of liquid, and from which a liquid depth can be deduced, is a time of flight for an optical pulse from an optical source to an optical detector.

The example of FIG. 11 includes a source and a detector positioned so as to emit and detect light through a base wall of a reservoir, when the reservoir is held vertically. The light propagates through the liquid to reach the liquid surface for reflection before the return path to the detector, also through the liquid. This arrangement is conceptually attractive since the time of flight is directly proportional to the liquid depth, so a longer time of flight represents a larger liquid depth. However, the light may undergo optical absorption during its propagation through the liquid, so that its intensity is reduced. It is therefore necessary to ensure that a sufficient amount of light is emitted by the source to leave a detectable amount to reach the detector after any absorption along the optical path through the liquid.

Figure 13:
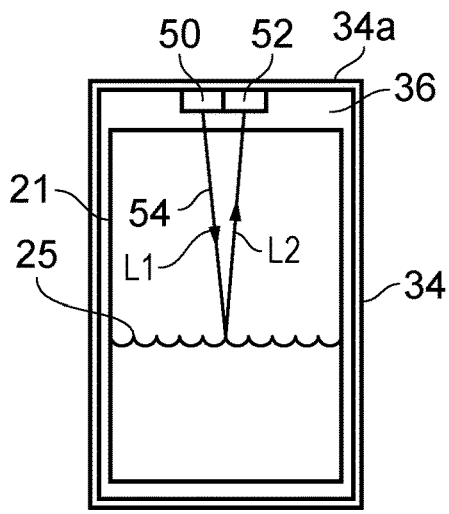
FIG. 13 shows a longitudinal cross-sectional view of another example liquid detection system.

FIG. 13 shows an alternative configuration using time of flight which avoids optical absorption in the liquid. In this example, the optical source 50 and the optical detector 52 are located on an upper wall 34a of a surrounding wall 34 defining a space 36 to receive a reservoir 21, so that light is emitted from the source 50 downwardly into the reservoir 21, and reflected upwardly from the surface of the liquid 25 to reach the detector 52. The principle of operation is the same as the FIG. 11 example, in that when the reservoir 21 is held vertically, reflection from the liquid surface creates an optical path from the source 50 to the detector 52, where the length of the optical path, and hence the time of flight for a light pulse travelling the optical path, varies with the position of the liquid surface, corresponding to the depth of the liquid 25. However, unlike the FIG. 11 example, the optical path lies wholly in the air space above the liquid, so the light avoids optical absorption in the liquid. The relevant speed of light is the speed in air, rather than the speed in the source liquid. Also, the relationship between time of flight and liquid depth is the inverse of that in the FIG. 11 example. A near-full reservoir has a liquid surface which is high, and close to the source and detector, so the optical path L=L1+L2 is short and the time of flight t is short. A near-empty reservoir has a liquid surface which is low, and far from the source and the detector, so the optical path L is longer and the time of flight is longer. Otherwise, derivation of a liquid depth from a measured time of flight can be the same as for the FIG. 11 example.

Figure 14:
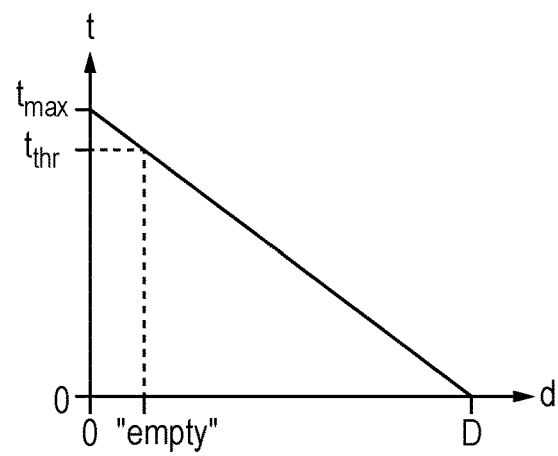
FIG. 14 shows a graph of an example response of the liquid detection system of FIG. 13.

FIG. 14 shows an example graph of a possible relationship between measured time of flight t and liquid depth d. Again, the relationship is linear, but inversely proportional, with a greater depth of liquid D giving a shorter measured time of flight. A full or near-full tank with liquid depth D gives a very short optical path and short time of flight, so a time of flight which is effectively zero will be measured. An empty tank with a liquid depth d of zero allows the light to propagate the full distance from the top to the bottom of the reservoir and back, giving a maximum optical path length of twice the reservoir depth, and corresponding maximum measurable time of flight $t_{max}$. The inner surface of the reservoir base wall may have a reflective coating to ensure reflection of the light back to the detector when the reservoir is empty. As in the previous example, a shallow liquid depth might be chosen as corresponding to an "empty" reservoir, with a corresponding threshold time of flight $t_{thr}$. Measured flight times longer than $t_{thr}$ can be reported as the reservoir being empty.

The FIGS. 11 and 13 examples utilize reflection of light at the liquid surface to obtain information regarding liquid depth by considering time of flight of a light pulse, where the reflection is arranged to be at or near to 180° to the incident light direction by having light incident on the liquid surface approximately perpendicularly. Other examples utilize light reflection from the liquid surface at non-perpendicular angles to derive information about the liquid surface position and hence liquid depth.

Figure 15:
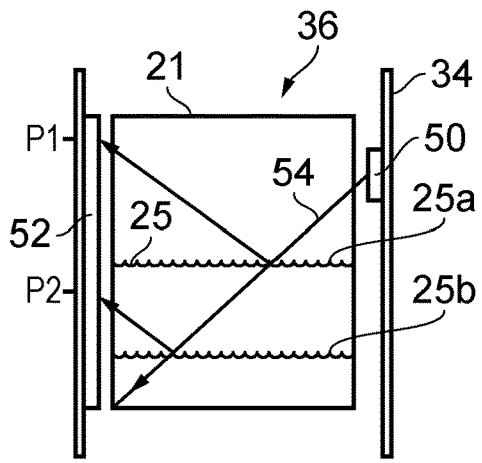
FIG. 15 shows a longitudinal cross-sectional view of still another example liquid detection system.

FIG. 15 shows a simplified schematic cross-sectional view of a system configured to utilize light reflection in this way. A surrounding wall 34 defines a space 36 for receiving a reservoir 21, and includes side walls adjacent the sides of the reservoir 21. An optical source 50 is mounted on an inner surface of the wall 34 at or near the top of the reservoir 21, and arranged to direct its emitted light into the interior of the reservoir at a downwardly sloping angle towards the opposite lower side of the reservoir 21. Accordingly, the optical path of the light 54 intercepts the surface of liquid in the reservoir 21 at a non-perpendicular angle of incidence for any depth of liquid. An optical detector 52 is mounted on an inner surface of the wall 34 on an opposite side of the reservoir to the source 50. The detector has an elongate configuration that extends over some or all of the reservoir's vertical depth direction in a plane parallel to the reservoir depth axis, and is able to spatially resolve any detected light such that the position (vertical height or depth) of the light as it is incident on the detector 52 can be determined. This might be achieved by an elongate array of discrete detectors or detector elements, or a detector comprising multiple detecting pixels, or any other format of optical detector that can resolve position.

Light 54 emitted from the source 50 enters the interior of the vertically oriented reservoir and traverses any empty air space above the liquid 25 held in the reservoir 21. At the liquid surface, some of the light will continue along the direct optical path towards the base of the reservoir, and some will be reflected from the surface back into the air space. Owing to the oblique angle of incidence, the reflected light is directed away from the source 50 and towards the detector 52 on the opposite side of the reservoir. The reflected light traverses the air space to the reservoir wall, is transmitted through the reservoir wall and reaches the detector 52 at a vertical position P, where it is detected. The vertical height or depth of the position P depends on the height or depth of the liquid surface, as can be appreciated from FIG. 15. The angles of incidence and reflection at the liquid surface which define the indirect optical path from source to detector taken by the reflected light are the same for any depth of liquid, but the depth of the liquid surface determines the position on the detector at which the reflected light arrives. A higher liquid level 25a reflects the light at a position close to the side of the reservoir 21 where the source 50 is mounted so the reflected light comprises a long part of the overall path length and the light is able to reach a high position P1 on the detector. Conversely a low light level 25b does not reflect the light until it is much closer towards the side of the reservoir 21 where the detector 52 is mounted. The reflected light comprises only a short part of the overall path length and the light reaches only a low position P2 on the detector 52. Appropriate calibration of the system can determine the relationship between detected light position and liquid depth, so that the liquid depth can be readily deduced once the position of the detected light is obtained from the detector 52. In this example, therefore, the characteristic of interest from which the liquid level can be deduced is the vertical or depth position at which the light is detected.

Figure 16:
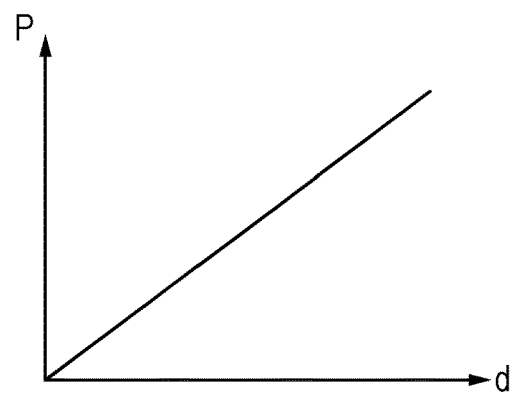
FIG. 16 shows a graph of an example response of the liquid detection system of FIG. 15.

FIG. 16 shows an example graph of a possible relationship between detected light position P as a height above the base of the reservoir, and the liquid depth D. The relationship is linear, with a increased depth of liquid producing a higher detection position. The source and detector can be positioned such at that for an empty reservoir, or a near-empty reservoir, no light is incident on the detector (either because there is no reflection in the total absence of liquid, or because for a very shallow depth of liquid the reflected light exits the reservoir below the lowest part of the detector), so a null response (no light detected) is interpreted as indicating an "empty" reservoir.

Note that the configuration of FIG. 15 may be inverted so that light is emitted in an upwardly sloping direction through any liquid in the reservoir, and reflected at the liquid surface from below. This is comparable with the inversely related operation of the examples in FIGS. 11 and 13. However, the non-perpendicular geometry of the reflected optical path means that the relationship between detected light position and liquid depth is not reversed compared to the FIG. 16 response. A large depth of liquid will produce a high detection position and a low depth of liquid will produce a low detection position, as in FIG. 16.

It will be apparent that other characteristics which can be induced in a light beam passing through liquid can be used to ascertain the presence or absence of liquid in a reservoir, or to determine an absolute quantity or depth of liquid in a reservoir or a proportional fill of a reservoir with liquid. Hence, a liquid detection system for a vapor provision system or device may be configured differently from the examples discussed so far. Other more minor modifications may also be made.

For example, while the optical source and optical detector have been described as being mounted on one or more surrounding walls that define a space or chamber for receiving at least a part of the reservoir, this is not essential. One or both of the source and the detector may alternatively be mounted externally onto the outer surface of the reservoir wall or walls, facing inwardly to emit light into the reservoir interior and receive light exiting the reservoir interior. Such an arrangement may be more suitable for ensuring correct positioning of the source and/or the detector relative to the reservoir. However, in vapor provision devices in which the reservoir is intended to be disposable (either alone or as part of a larger component such as a cartomizer), it may be more convenient to mount the source and the detector on surrounding walls(s) which form part of a reusable component of the device (such as a power and/or control unit). This will reduce waste and keep device cost down.

In arrangements where the source and detector are mounted on a surrounding wall defining a chamber that accommodates the reservoir, this surrounding wall may be comprised in either a cartomizer section of the vapor provision device or in a power/control section, in designs where these sections are separable. The chamber may be defined partly by one or more walls included in the cartomizer and partly by one or more walls included in the control unit. Alternatively the vapor provision device may be unitary, and not designed for separation into distinct components. The reservoir and any surrounding walls may be differently shaped and configured than the examples illustrated in the accompanying drawings, which are simple schematics only and not intended to be limiting as regards size and shape of the various components.

The source and detector need not be positioned relative to each other precisely as illustrated, either. For any detected characteristic, it is sufficient that the optical path from the source to the detector passes through the interior storage volume of the reservoir in some way that gives a path length long enough for the required characteristic to be acquired by the light. The optical path need not traverse a diameter or full width of the reservoir, for example, but may pass through a smaller portion of the volume. In some examples, the optical path will need to avoid obstacles such as a central air passage through an annular reservoir, so the source and the detector can be positioned accordingly.

The liquid detection system may be under the control of a dedicated controller, or under the control of a control unit that operates other components of the vapor provision device, such as controlling the supply of electrical power to a heating element to generate vapor. A dedicated controller can communicate with any separate control unit for integrated operation of the vapor provision device. The terms "controller", "processor", circuitry", "control unit" and the like include any combination of hardware, software, firmware, processors, memory, electrical circuitry and the like that can be configured to implement the required operation of the liquid detection system.

Figure 17:
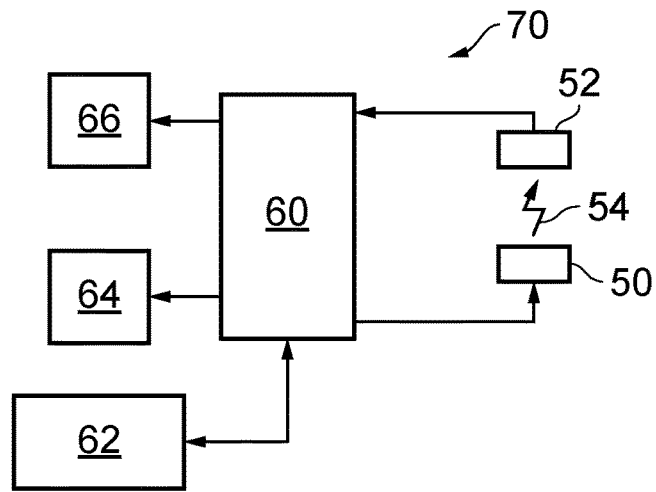
FIG. 17 shows a schematic example circuit diagram for implement a liquid detection system.

FIG. 17 shows a simple schematic circuit diagram of an example liquid detection system for a vapor provision device. A controller 60 controls operation of the system 70. The controller 60 is connected to/connectable to/in communication with a control unit 62 configured to control other elements of a vapor provision device. The control unit 62 may send a signal to the controller 60 when a liquid detection measurement is required (in response to a user request, for example, or when a reservoir has been replaced or refilled), or the controller 60 may initiate a measurement itself. The controller 60 sends a control signal to an optical source 50 to cause the optical source 50 to emit the required light 54 into the chamber where a reservoir will be housed (reservoir not shown in FIG. 17 as it is not a part of the liquid detection system per se). After traversing the reservoir interior space the light 54 may be detected by an optical detector 52. The output of the detector 52, indicating light detected, is sent to the controller 60 for processing to determine the relevant characteristic of the light and deduce from that result the presence or absence of liquid, or a depth of liquid, according to the various examples described. This information may then be used in any of several ways. The controller 60 may communicate it to the control unit 62 for use in control of the rest of the vapor provision device. For example, if it is determined that the reservoir is empty, the control unit may cease operation of the vapor generating element, such as to avoid overheating of a heating coil. Also, the controller 60 may communicate the liquid detection result to a display 64 or other user output device that can present the liquid level information to the user. This may be a simple warning light for illumination when the reservoir is determined to be empty, and possibly a second light for illumination to indicate that the reservoir is not empty. A liquid crystal display or other screen display may be used to present more detailed information, such as a percentage of liquid remaining, calculated from a determination of the depth of liquid in the reservoir. Also, the system 70 may include a communication interface 66 by which the controller can send the liquid detection result to an external recipient. For example, detection of a near-empty reservoir can be communicated to an ordering system for dispatch of a replacement cartomizer section or a new bottle of source liquid. Communication by the interface 66 may be wired (such as by a USB connection) or wireless (such as by a Bluetooth connection or infrared or radio frequency signaling). The various control components 60, 62, 64 and 66 are shown as individual modules in FIG. 17, but this is for simplicity, and in reality the various functions provided may be combined into or divided between one or more modules or components as desired.

The optical source and the optical detector may be any suitable optical elements capable of emitting light at the required wavelength or wavelengths and detecting light at that same wavelength or wavelengths. They may be light emitting diodes, laser diodes, and photodetectors, for example. In some arrangements, a directional beam of light is required so that emitted light is directed along the required optical path, so the optical source should be configured accordingly. In some arrangements, in particular systems that measure time of flight, a short pulse of light is required, rather than a continuous output, so an optical source capable of pulsed (probably ultrashort pulsed) output can be selected. The detector may be provided with a filter to reduce detection of stray or ambient light that has not originated from the optical source, if its response bandwidth is not well-matched to the source emission bandwidth. The emission wavelength of the light source may be selected to be visible or not, according to convenience and circumstances. If the reservoir is fully enclosed in an opaque housing, the liquid detection system light will not be discernible from the exterior of the vapor provision device so the visibility of the light is not a relevant consideration. If the reservoir is externally visible, including transparent walls so that its interior can be discerned by the user, a choice between visible and non-visible (infrared and ultraviolet) light is required. A visible wavelength provides visual feedback for the user that the light detection system is operational, which may be useful in designs where the user can choose to activate a light detection measurement (by a button or switch on the exterior of the vapor provision device, for example). If the light detection system is activated automatically such as on a timed basis for regular measurements or in response to other actions within the vapor provision device, a non-visible wavelength may be preferred for more discrete operation.

The wavelength should also be selected in combination with properties of the source liquid so that a detectable magnitude of interaction for the characteristic of interest will take place when the light traverses liquid in the reservoir. For example, an appreciable level of optical absorption at the emitted wavelength should arise in the liquid for the example systems of FIGS. 5-9, so the respective colors of the light and the liquid should be chosen accordingly. The liquid may also be designed to provide a good response for the characteristic of interest, such as being provided with a high density of scattering centers for the example system of FIG. 10.

While the various example detection systems have been described in the context of a complete vapor provision system, a detection system according to the present disclosure may be included or provided as part of a complete vapor provision system, as part of a cartomizer unit or module for a vapor provision system, as part of a control or power unit or module for a vapor provision system, in conjunction with a reservoir for use in a vapor provision system, such as in a cartridge, or as a detection system per se, such as for retro-fitting to an existing vapor provision system or part thereof. Thus, all features of a detection system disclosed herein are applicable to a complete vapor provision system, a cartomizer, a cartridge, a control unit, or to a aerosolizable substrate material detection system alone.

Figure 18:
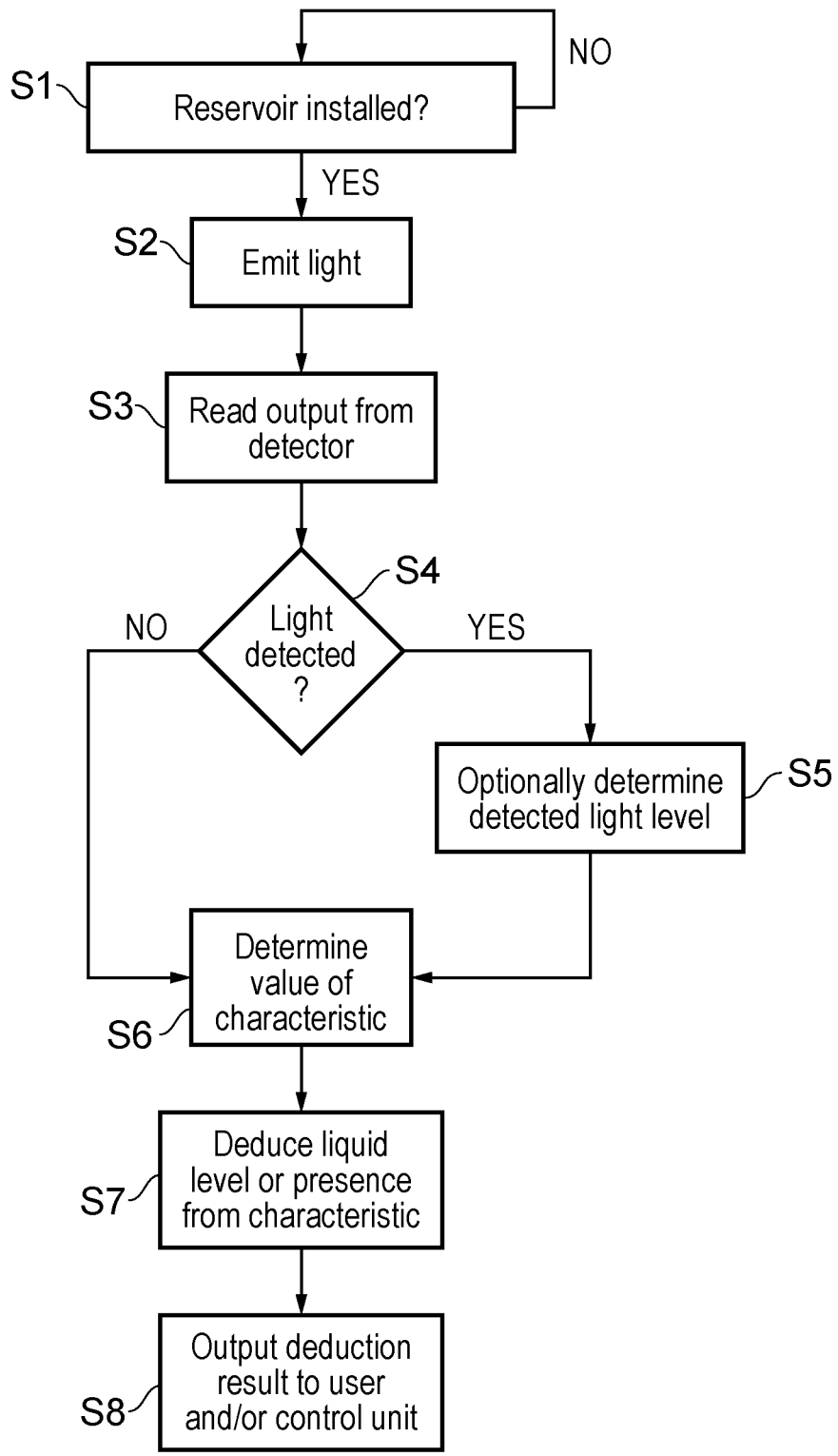
FIG. 18 shows a flow chart of an example method for liquid detection.

FIG. 18 shows a flow chart of steps in an example method of liquid detection in a vapor provision system. In optional 51, a system such as that in the examples of FIGS. 4 to 17 but not limited thereto, can check that a reservoir is installed in a vapor provision device or system preparatory to liquid detection. If no reservoir is found, the method loops back to repeat 51 at a later time. If a reservoir is found to be installed, the method proceeds to S2 in which an optical source emits light into the reservoir (initiated automatically or in response to a user request). Depending on the liquid detection technique employed and the presence or absence of liquid, some or all of the emitted light may reach an optical detector. The output of the detector is read out or otherwise obtained or extracted in S3. In S4, it is determined from the detector output whether or not light has been detected. A null result of no light detected is meaningful in some arrangements, as discussed above. If light is detected, an optional S5 may be performed in which the amount, level or intensity of the detected light is determined, in contrast with a simple determination that light has or has not been detected. In S6, the result of no light, light and/or intensity of light is used to determine the characteristic of the light upon which the detection approach is based. As described, examples of characteristics include an amount of light reaching the detector from the source, a time of flight for a pulse of light to travel from the source to the detector, and a position of a detected beam of light relative to the reservoir. Note that the characteristic of an amount of light includes both a variable light intensity from which a depth of liquid can be deduced (as in the FIGS. 7 and 9 examples), and a distinction between light and no light regardless of absolute amount (as in the FIGS. 5A, 5B and 10 examples). Once the value of the characteristic is obtained, the method advances to S7 in which the characteristic is used to deduce a depth or level of liquid in the reservoir or to deduce the simpler result that liquid is present or absent (indicating that the reservoir is either full/not empty or empty/near empty). In S8, the liquid detection result deduced in S7 is output for use, such as being displayed or otherwise communicated to a user, communicated externally of the vapor provision device, or passed to a control unit within the vapor provision device that controls operation of the device's other components.

In conclusion, in order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein. The disclosure may include other inventions not presently claimed, but which may be claimed in future.

The invention claimed is:

1. A vapor provision system comprising:
    a reservoir defining a storage volume to hold aerosolizable substrate material;
    one or more walls encompassing a space for receiving at least a part of the reservoir; and
    an aerosolizable substrate material detection system comprising:
        an optical source located externally of the reservoir on the surface of the one or more walls to face inwardly into the space, and operable to emit light into the storage volume,
        an optical detector located externally of the reservoir on a surface of the one or more walls to face inwardly into the space and operable to detect light emitted by the optical source that has traversed an optical path through the storage volume, and
        a controller configured to determine a characteristic of the light detected by the optical detector and deduce information regarding a depth of aerosolizable substrate material in the storage volume from the determined characteristic of the light,
        wherein the optical source is located at a source depth relative to the reservoir and the optical detector is located to detect light emitted by the optical source that has been scattered into an indirect optical path by aerosolizable substrate material in the storage volume, and the controller is configured to deduce that the depth of aerosolizable substrate material is above the source depth if the amount of light detected is a first amount and the depth of aerosolizable substrate material is below the source depth if the amount of light detected is a second amount which is less than the first amount.

2. The vapor provision system according to claim 1, wherein the vapor provision system comprises a cartomizer and a control unit separably connectable to one another, and wherein the reservoir is comprised in the cartomizer, and the optical detector, the optical source and the controller are comprised in the control unit.

3. The vapor provision system according to claim 1, wherein the aerosolizable substrate material comprises a liquid.

4. The vapor provision system according to claim 1, wherein the aerosolizable substrate material comprises a gel.

5. The vapor provision system according to claim 1, wherein the storage volume is configured to hold the aerosolizable substrate material as a free-flowing material.

6. A vapor provision system comprising:
   a reservoir defining a storage volume to hold aerosolizable substrate material;
   one or more walls encompassing a space for receiving at least a part of the reservoir; and
   an aerosolizable substrate material detection system comprising:
      an optical source located externally of the reservoir on the surface of the one or more walls to face inwardly into the space, and operable to emit light into the storage volume,
      an optical detector located externally of the reservoir on a surface of the one or more walls to face inwardly into the space and operable to detect light emitted by the optical source that has traversed an optical path through the storage volume, and
      a controller configured to determine a characteristic of the light detected by the optical detector and deduce information regarding a depth of aerosolizable substrate material in the storage volume from the determined characteristic of the light,
   wherein the optical detector is located to detect light emitted by the optical source that has been reflected into an indirect optical path from a surface of aerosolizable substrate material in the storage volume.

7. The vapor provision system according to claim 6, wherein the optical detector is located to detect the light emitted by the optical source that has traversed the storage volume via a direct optical path so as undergo optical absorption by any aerosolizable substrate material along the direct optical path, the characteristic of the light being an amount of light detected by the optical detector.

8. The vapor provision system according to claim 7, wherein the optical source and the optical detector are located at a same detection depth relative to the reservoir such that a depth of aerosolizable substrate material in the storage volume above the detection depth places aerosolizable substrate material along the direct optical path to produce optical absorption of the emitted light, and the controller is configured to deduce that the depth of aerosolizable substrate material is below the detection depth if the amount of light detected is a first amount and that the depth of aerosolizable substrate material is above the detection depth if the amount of light detected is a second amount which is smaller than the first amount.

9. The vapor provision system according to claim 8, wherein the detection depth is at a base of the reservoir and the controller is configured to deduce that the storage volume is holding no aerosolizable substrate material if the first amount of light is detected.

10. The vapor provision system according to claim 8, further comprising additional pairs of an optical source and an optical detector, each of the additional pairs located at a different detection depth, and wherein the controller is configured to deduce that the depth of aerosolizable substrate material in the storage volume does not exceed the detection depth of a highest optical detector at which the second amount of light is detected.

11. The vapor provision system according to claim 7, wherein the optical source is located at a source depth relative to the reservoir and the optical detector is located at a detector depth relative to the reservoir, the source depth and the detector depth being different, such that a depth of aerosolizable substrate material in the storage volume between the source depth and the detector depth produces an amount of optical absorption of the emitted light that is proportional to the depth of the aerosolizable substrate material, wherein the controller is configured to use the proportionality to deduce the depth of the aerosolizable substrate material from the amount of light detected by the optical detector.

12. The vapor provision system according to claim 6, wherein the optical source and the optical detector are located substantially coincidentally to form an indirect optical path substantially parallel to a depth direction of the reservoir, and the characteristic of the light is a propagation time of a pulse of light emitted from the optical source to travel from the optical source to the surface of the aerosolizable substrate material to the optical detector, and the controller is configured to deduce the depth of the aerosolizable substrate material from the propagation time.

13. The vapor provision system according to claim 6, wherein the optical detector is configured to spatially resolve a position at which light emitted from the optical source is detected, and the optical source is arranged to emit light to be incident on the surface of the aerosolizable substrate material at a non-perpendicular angle such that the reflected light is incident on the optical detector at a position that varies with the depth of the aerosolizable substrate material, wherein the characteristic of the light is the detected position on the optical detector, and the controller is configured to deduce the depth of the aerosolizable substrate material from the detected position.

* * * * *